United States Patent [19]

Smith et al.

[11] Patent Number: 5,702,683
[45] Date of Patent: Dec. 30, 1997

[54] NUCLEAR MAGNETIC RESONANCE CONTRAST AGENTS

[75] Inventors: Paul H. Smith; James R. Brainard; Gordon D. Jarvinen; Robert R. Ryan, all of Los Alamos, N. Mex.

[73] Assignee: The United States of America as represented by the United States Department of Energy, Washington, D.C.

[21] Appl. No.: 643,092

[22] Filed: Jan. 22, 1991

Related U.S. Application Data

[63] Continuation of Ser. No. 301,678, Jan. 24, 1989, abandoned.

[51] Int. Cl.⁶ .............................. A61B 5/055; C07F 5/00; G01N 24/00
[52] U.S. Cl. .......................... 424/9.361; 534/10; 534/15; 534/16; 436/173
[58] Field of Search ........................... 534/15, 16, 10; 424/9, 9.361, 9.362, 9.363; 436/173; 128/653 A, 653 AF, 653 CA, 653.2, 653.4

[56] References Cited

U.S. PATENT DOCUMENTS

| | | | |
|---|---|---|---|
| 3,930,867 | 1/1976 | Bigelow | 96/107 |
| 4,639,365 | 1/1987 | Sherry | 424/9 |
| 4,647,447 | 3/1987 | Gries et al. | 424/9 |
| 4,687,658 | 8/1987 | Quay | 424/9 |
| 4,687,659 | 8/1987 | Quay | 424/9 |
| 4,719,098 | 1/1988 | Weinmann et al. | 424/9 |
| 4,746,507 | 5/1988 | Quag | 424/9 |
| 4,749,560 | 6/1988 | Elgavish | 424/9 |

OTHER PUBLICATIONS

J. F. Desreux et al., "Highly Stable Lanthanide Macrocyclic Complexes: in Search of New Contrast Agents for NMR Imaging," Nucl. Med. Biol. 15, No. 1, 9–15 (1988).
Susan C. Jackels et al., "Paramagnetic Macrocyclic Complexes as Contrast Agents for MR Imaging: Proton Nuclear Relaxation Rate Enhancement in Aqueous Solution and in Rat Tissues," Magn. Res., 525–530 (1986).
Randall B. Lauffer, "Paramagnetic Metal Complexes as Water Proton Relaxation Agents for NMR Imaging: Theory and Design" Chem. Rev. 87, 901–927, (1987).
L. De Cola et al., "Hexaaza Macrocyclic Complexes of the Lanthanides," Inorg. Chem. 25, 1729–1732 (1986).
Wanda Radecka–Paryzek, "The Template Synthesis and Characterization of Hexaaza 18–Membered Macrocyclic Complexes of Cerium(III), Praseodymium(III) and Neodymium(III) Nitrates," Inorg. Chem. Acta 109, L21–L23 (1985).
Khalil K. Abid et al., "Lanthanide Complexes of Some Macrocyclic Schiff Bases Derived from Pyridine–2,6–dicarboxaldehyde and alpha,omega,–Primary Diamines," Inorg. Chem. Acta 95, 119–125 (1984).
L. De Cola et al., "Metal–templated Synthesis of Novel Macrocyclic Complexes of the Uranyl Ion," Inorg. Chem. Acta 110, L1–L2 (1985).
Ata M. Arif et al., "Synthesis and Structure of Lanthanide Complexes of a Mixed Donor Macrocyclic Ligand," Inorg. Chem Acta 109, 179–183 (1985).
Khalil K. Abid et al., "The Synthesis of Macrocyclic Lanthanide Complexes Derived from 2,5–Furandial–dehyde and alpha,omega, alkanediamines," Inorg. Chem Acta 82, 223–226 (1984).
J. D. Julius Backer–Dirks et al., "Preparation and Properties of Complexes of Lanthanides and a Hexadentate Nitrogen–donor acrocycle: X–Ray Crystal Structure of the Comple [La(NO₃)₃L]," J. C. S. Chem. Comm., 774–775 (1979).
Khalil K Abid et al., "The Template Synthesis and Crystal and Molecular Structure of a Sexidentate Schiff–base Macrocyclic Complex of Samarium(III), [Sm(C₁₈H₁₈N₆) (NO₃) (OH) (H₂O)]NO₃ 2MeOH," J. Chem. Soc. Dalton Trans., 351–354 (1984).
Genglin Wang, et al., "Lanthanide Complexes with Eighteen–Membered Hexaaza Macrocyclic Ligands" (Dep. Chem., Nankai Univ., Tianjin, Peop. Rep. China). Gaodeng Xuexiao Huaxue Xuebao (1984), 5(3), 281–6 (Ch).

*Primary Examiner*—John Kight
*Assistant Examiner*—Michael G. Hartley
*Attorney, Agent, or Firm*—Richard J. Cordovano; Samuel M. Freund; William R. Moser

[57] ABSTRACT

A family of contrast agents for use in magnetic resonance imaging and a method of enhancing the contrast of magnetic resonance images of an object by incorporating a contrast agent of this invention into the object prior to forming the images or during formation of the images. A contrast agent of this invention is a paramagnetic lanthanide hexaazamacrocyclic molecule, where a basic example has the formula $LnC_{16}H_{14}N_6$. Important applications of the invention are in medical diagnosis, treatment, and research, where images of portions of a human body are formed by means of magnetic resonance techniques.

6 Claims, 2 Drawing Sheets

NUCLEAR MAGNETIC RESONANCE CONTRAST AGENTS

This is a Continuation of application Ser. No. 07/301,678 filed Jul. 24, 1989, now abandoned.

The invention was made with government support under Contract No. W-7405-ENG-36 awarded by the U.S. Department of Energy to The Regents of the University of California. The government has certain rights in the invention.

BACKGROUND OF THE INVENTION

This invention relates to the field of nuclear magnetic resonance imaging and nuclear magnetic resonance spectroscopy, also known simply as magnetic resonance imaging (MRI) and magnetic resonance spectroscopy (MRS). MRI and MRS are particularly useful in medical research and diagnosis. MRI may be used in addition to x-ray imaging.

MRI is used to obtain multiplanar images of objects and, most commonly, is used to study living organisms. MRI images depict the locations and concentrations of a single component, such as hydrogen nuclei, in an object. MRS provides information on chemical composition of substances. MRI shows the spatial distribution of a particular chosen species of atomic nuclei, while MRS distinguishes between different types of molecules which contain a common atomic nucleus. At the present time, since MRI is in much wider use than MRS, the discussion herein will focus primarily on MRI. However, those skilled in the art will appreciate that much of the discussion herein which deals with MRI also applies to MRS.

Since protons are the most abundant and sensitive nuclei in biological tissues, a majority of medical applications of MRI utilize images of protons. These MRI images primarily reflect the distribution of water in a human body, since the protons in biological tissue are present mainly as water. MRI images have an appearance which is similar to x-ray computerized tomography scan images, but MRI images are based on differences in water content and differences in relaxation rates of water in various body tissues rather than on differences in the absorption of x-rays between various tissues of the body.

One of the advantages of MRI is that it does not use ionizing radiation and therefore is considered to be safer than X-ray computer tomography. In addition, the intensity and contrast in MRI is subject to many more variables reflecting tissue structure and health, than in x-ray CT. While not all of these variables are completely understood at present, MRI applications are increasing rapidly, and MRI is already the preferred imaging method for diagnosis of multiple sclerosis and other diseases.

MRI uses a smooth nonuniform magnetic field, or magnetic field gradient, and radio frequency radiation to locate the positions of atomic nuclei in space. Many nuclei have a property called nuclear spin, which causes the nuclei to behave like tiny bar magnets when they are placed in a magnetic field. The spin of the nuclei can align either parallel to the magnetic field or anti-parallel to the magnetic field, and transitions between these two states can be induced and observed by means of radio frequency radiation. Nuclei in a ground state have nuclear spin oriented anti-parallel to the magnetic field while nuclei in an excited state have nuclear spin in a parallel orientation. The frequency of the radiation that induces transitions between the ground and the excited states can be related to the location of the nuclei in the magnetic field gradient.

The properties of body tissue that are reflected most directly in MRI images are the amount of water contained in tissue (proton density) and the rates at which the water protons return to their ground state energy levels. These rates are known as relaxation rates. MRI images may be obtained using data acquisition and processing methods such that tissues which contain a great deal of water, such as kidneys, appear white, while other tissues containing less water, such as tendons, appear dark. Other acquisition and processing techniques may be used to obtain images where tissues containing water which returns rapidly to the ground state energy level (relaxes rapidly) appear light, while tissues containing water which relaxes slowly appear dark.

While many tissues in diseased states exhibit differences in proton density and relaxation rates naturally, it is desirable to use MRI contrast agents to further enhance the differences in MRI intensity between various tissues and between healthy and diseased tissue. The relaxation rates of water in body tissue may be increased by adding paramagnetic metal ions (ions with unpaired electrons) to the tissue. The unpaired electrons in these metals greatly increase the relaxation rates of nearby water protons. Thus, where paramagnetic metals (such as gadolinium), are taken up in a greater amount by certain tissues, the relaxation rates of water in those tissues are increased, compared to tissues which take up a lesser amount of the metal, and the tissues appear light in MRI images. A substance, such as one of these paramagnetic metals, which causes tissue to appear lighter or darker in MRI images as a result of its presence is termed a contrast agent. Desirable properties for a contrast agent include high relaxivity, low toxicity, and the ability to distinguish different tissues or pathologies.

Paramagnetic metal ions are toxic to living organisms. In order to reduce toxicity, the effective concentration of a free metal ion is reduced by using complexes of paramagnetic metals with organic ligands. A complex of gadolinium with diethylenetriaminepentaacetic acid (GdDTPA) is currently the most commonly used contrast agent because of its large magnetic moment and relatively low toxicity. Also, GdDTPA is currently the only MRI contrast agent licensed for clinical use in humans. The high stability constant ($K \sim 10^{22}$) of GdDTPA greatly reduces toxic effects of Gd(III). However, a factor limiting its effectiveness as a relaxation agent is the availability of only one water coordination site in the complex. Other polyamino carboxylate ligands having fewer groups which coordinate to Gd have been suggested as potential MRI contrast agents on the theory that the available sites on the paramagnetic metal for water exchange will be increased by reducing the number of metal-ligand bonds. Although these complexes are better relaxation agents than DTPA, they are less stable and often too toxic for medical use. The challenge is to design paramagnetic metal complexes which have multiple water coordination sites and yet remain intact under physiological conditions.

As mentioned above, hydrogen nuclei are most often utilized in magnetic resonance imaging, but other nuclei may be used, such as sodium and phosphorus. For example, there are applications in which it is desirable to determine the location and concentration of adenosinetriphosphate (ATP) in body tissue; this can be accomplished by use of particular radio frequencies which excite the phosphorous atom nuclei of ATP. ATP is important in energy utilization in the human body.

MRS provides information about the chemical composition of materials, both living and nonliving. MRS is also applied in medical research and diagnosis, and contrast agents of this invention will find applications in MRS.

BRIEF SUMMARY OF THE INVENTION

This invention is a family of contrast agents for use in magnetic resonance imaging and a method of enhancing the contrast of magnetic resonance images of an object by incorporating a contrast agent of this invention into the object prior to forming the images or during formation of the images. Important applications of the invention are in medical diagnosis, treatment, and research, where images of portions of a human body are formed by magnetic resonance techniques.

Contrast agents of this invention are depicted in FIG. 1. A contrast agent of this invention may be described as a paramagnetic lanthanide hexaazamacrocyclic molecule, said molecule being comprised of a paramagnetic lanthanide atom having positive charges within a central ring structure consisting of six nitrogen atoms, where said molecule is further comprised of two pyridine rings, two substructures, and four linking carbon atoms, each pyridine ring containing one of said six nitrogen atoms and each substructure containing two of said six nitrogen atoms, where each substructure is linked to each pyridine ring by means of a linking carbon atom which is double-bonded to a nitrogen atom of a substructure and single-bonded to a carbon atom of a pyridine ring, where each substructure contains at least one carbon atom in addition to the two nitrogen atoms, and where substituent groups including hydrogen atoms, each denoted by R, are attached to the free valences of the carbon atoms of the molecule and may also coordinate with the lanthanide ion.

BRIEF DESCRIPTION OF THE DRAWINGS

The structural formulas of FIG. 1 depict and define contrast agents of this invention. FIGS. 1B through 1I define portions of the molecule of FIG. 1A. The symbol consisting of two nitrogen atoms connected by an arc, which appears in two places in FIG. 1A and is shown in FIGS. 1B and 1C, may be any one of the five structures depicted in FIGS. 1D through 1H. That is, either of the two nitrogen atoms connected by an arc shown in FIG. 1A represents any one of the five structures of 1D through 1H. Further, as shown in FIG. 1I, an "R" of FIGS. 1A, 1D, 1E, 1F, 1G, and 1H is either a hydrogen atom or a substituent group (for example, an alkyl), where the substituent groups are those listed herein.

DETAILED DESCRIPTION OF THE INVENTION

Figure 1A:
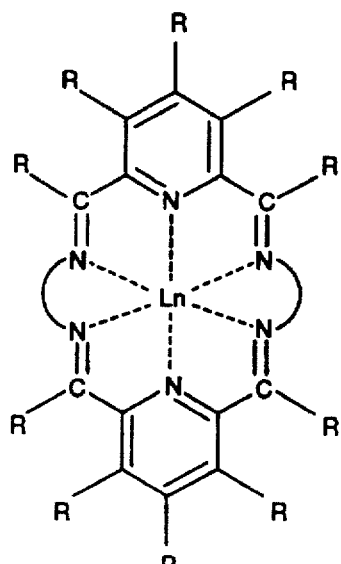
FIG. 1A is the general structural formula of a cationic lanthanide hexaazamacrocyclic molecule.
Figure 1D:
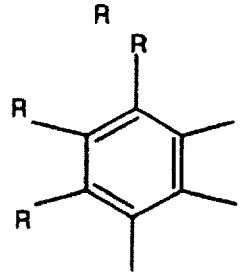
Figure 1E:
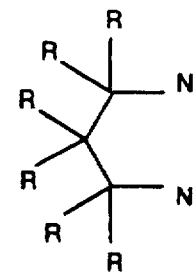
Figure 1I:
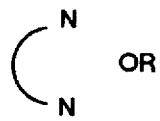
Figure 1I:
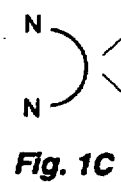
Figure 1F:
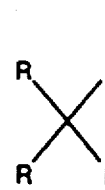
Figure 1G:
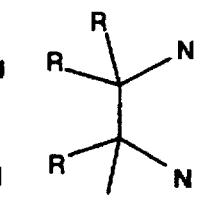
Figure 1H:
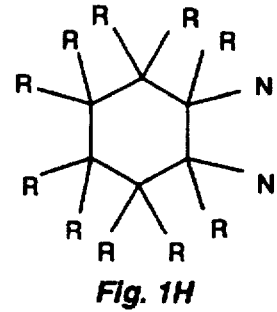

The compounds of this invention are depicted in FIG. 1, as explained above under "Brief Description of the Drawings." Note that there is a departure from standard symbology in FIG. 1A, in that the symbol "C" is used to show four of the carbon atoms, while other carbon atoms are depicted in the standard manner. This is done because these four carbon atoms are specifically mentioned in the verbal description of the compounds of this invention as being "four linking carbon atoms." The verbal description may be found under "Brief Description of the Invention."

The family of contrast agents of this invention may be referred to as paramagnetic lanthanide hexaazamacrocycles, which may be abbreviated as LnHAMs. They also may be termed paramagnetic lanthanide Schiff's Base macrocyclic complexes or Schiff's Base macrocycles or metal chelates of macrocyclic polyamines.

Figure 2:
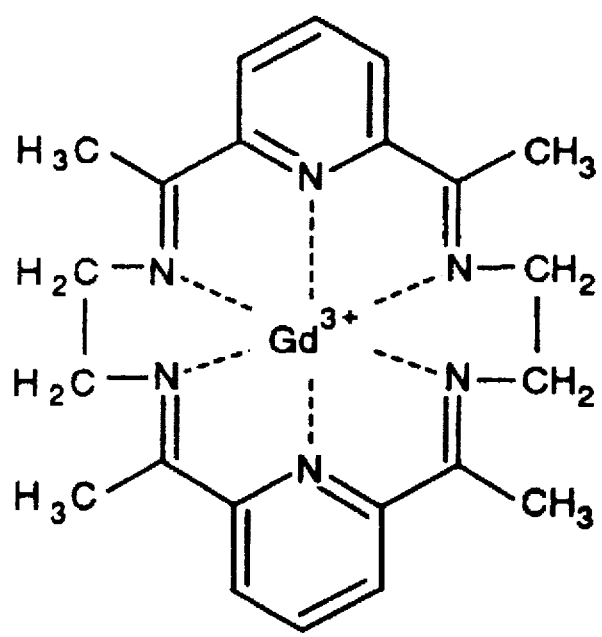
FIG. 2 depicts the structural formula of a single contrast agent of this invention where the lanthanide is gadolinium and the arc connecting a pair of nitrogen atoms represents two methylene groups as shown in FIG. 1G (where the R's of FIG. 1G all represent hydrogen atoms).

The term GdHAM(2) is used herein to denote the gadolinium hexaazamacrocycle of FIG. 2, since conventional names for specific compounds of this invention would be extremely cumbersome.

GdHAM(2)(OAc)$_2$Cl.4H$_2$O was synthesized by the method of De Cola et al. (see Item 1 of the list of articles presented below). The formula of GdHAM(2) is GdC$_{22}$H$_{26}$N$_6$ and that of OAc is (OCOCH$_3$)$^-$. Elemental analysis was performed and was consistent with the formula GdC$_{26}$H$_{32}$N$_6$O$_4$Cl.4H$_2$O, which represents the combination of the cation GdHAM(2) and the counter ion consisting of two (OAc)$^-$ groups and one chloride atom. The analogous complexes of europium and dysprosium were also synthesized. The number of water molecules coordinated with EuHAM(2) in solution averages between three and four, as determined by luminescence lifetime measurements.

The inventive compounds are either neutral or charged when they are dissolved in water. One or more substituent groups, as defined below, may be charged. It is believed that the corresponding counter ions play no part in the utility of the compounds as contrast agents and that the counter ions may be any compatible atoms or groups. In aqueous solution, GdHAM(2) has a positive valence of 3.

It is expected that any paramagnetic lanthanide may be used in the present inventive family of contrast agents. These paramagnetic lanthanides are cerium, dysprosium, erbium, europium, gadolinium, holmium, neodymium, praeseodymium, promethium, samarium, terbium, thulium, and ytterbium. Usually, the lanthanide will be in the trivalent state. Also, it is expected that europium with two positive charges and terbium with four positive charges may be used.

The symbol "R" is used in FIG. 1 to represent a hydrogen atom or a substituent group. Groups which may be substituent groups on the structures depicted in FIG. 1 include alkyl, alkoxy, acyl, aroxy, alkylamine, aryl, hydroxy, aryloxy, amine, carboxylate, phosphate, sulfonate, and other similar groups. Substitutions of these groups may be made by one skilled in the art in order to modify properties of the inventive contrast agents, such as solubility, tissue specificity, toxicity, and relaxivity.

A measure of effectiveness of a relaxation agent is the relaxivity, which is defined as the change in solvent relaxation rate per concentration unit of the relaxation agent. The relaxivity of GdHAM(2) in aqueous solution is 9.7 sec$^{-1}$ mM$^{-1}$ at 0.47 T. In comparison, the relaxivities of Gd aquo ion and GdDTPA are 9.1 and 4.1 sec$^{-1}$ mM$^{-1}$, respectively, both at 0.47 T.

A preliminary toxicity study was performed on GdHAM(2) using a sensitive cell growth inhibition test. Although we had evidence that GdHAM(2) was hydrolytically stable, it was necessary to evaluate the cellular toxicity of the intact complex. This test determines the biological toxicity of a compound by measuring the inability of cells to grow in the presence of the test compound. The toxicity of GdHAM(2) was compared to that of GdDTPA. Cell culture media containing 0.25 mM GdHAM(2) was added to mouse tumor tissue culture cells (EMT 6) growing in a petri dish. The same procedure was followed using 0.25 mM GdDTPA in a second petri dish and an equal volume of sterile saline solution in a third petri dish. Several sets of three similar petri dishes in each set were prepared. At 24, 48, and 72 hours after adding the media containing the three different compounds (GdHAM(2), GdDPTA, and saline solution), the number of living cells in each petri dish was determined using a microscope. At each time point, the toxic effect of the compounds was measured by comparing the number of living cells in the petri dishes containing GdHAM(2) and GdDTPA to the number of living cells in the control petri dish. At each time point, GdHAM(2) and GdDTPA inhibited the growth of cells as compared to the sterile saline, but it could be clearly seen that the toxic effect of GdHAM(2) was considerably less than of GdDTPA.

The specificity of GdHAM(2) for tumors was demonstrated by MRI of canine glioma tumors in rats. Tumors were implanted into the flanks of two rats by injection of one million canine glioma cells in each rat. Seven days later, one rat was imaged using GdHAM(2) as a contrast agent and the other was imaged using GdDTPA. A General Electric Signa 1.5T imager was used. T1 weighted spin echo images of the rats were obtained at 5, 12, 20, and 24 minutes after injection of doses having the same concentrations of GdHAM(2) and GdDTPA into the jugular veins of the rats. The GdHAM(2) image and the GdDTPA image taken 5 minutes after injection appeared to be about the same. However, comparing the images taken at 12, 20 and 24 minutes after injection shows that the tumor images of the GdHAM(2)-treated rat are significantly brighter than the tumor images of the GdDTPA-treated rat. In addition to the increased brightness, these results suggest that washout of GdHAM(2) from the tumor is slower than washout of GdDTPA. Slower washout is an advantage in clinical imaging, since it is difficult to obtain high contrast MRI images on low field MRI instruments in only 5 minutes. In addition, the images, showed no indication that GdHAM(2) is localized in the kidneys or liver, which are sites of high toxicity of contrast agents.

The complexes of this invention are prepared from a lanthanide salt, two equivalents of a diamine, and two equivalents of a diketone or dialdehyde in a template condensation reaction in which the reactants form a macrocycle around the lanthanide ion. Those skilled in the art are familiar with such reactions and the following articles also provide methods of making the compounds which are the contrast agents of this invention.

1. L. De Cola et al., "Hexaaza Macrocyclic Complexes of the Lanthanides," Inorg. Chem. 25, 1729–1732 (1986).

2. Wanda Radecka-Paryzek, "The Template Synthesis and Characterization of Hexaaza 18-Membered Macrocyclic Complexes of Cerium(III), Praeseodymium(III) and Neodymium(III) Nitrates," Inorg. Chem. Acta 109, L21–L23 (1985).

3. Khalil K. Abid et al., "Lanthanide Complexes of Some Macrocyclic Schiff Bases Derived from Pyridine-2,6-dicarboxaldehyde and alpha,omega,-Primary Diamines," Inorg. Cheim. Acta 95, 119–125 (1984).

4. L. De Cola et al., "Metal-templated Synthesis of Novel Macrocyclic Complexes of the Uranyl Ion," Inorg. Chem. Acta 110,L1–L2 (1985).

5. Ata M. Arif et al., "Synthesis and Structure of Lanthanide Complexes of a Mixed Donor Macrocyclic Ligand," Inorg. Chem Acta 109, 179–183 (1985).

6. Khalil K. Abid et al., "The Synthesis of Macrocyclic Lanthanide Complexes Derived from 2,5-Furandial-dehyde and alpha,omega,-alkanediamines," Inorg. Chem Acta 82, 223–226 (1984).

7. J. D. Julius Backer-Dirks et al., "Preparation and Properties of Complexes of Lanthanides and a Hexadentate Nitrogen-donor Macrocycle: X-Ray Crystal Structure of the Complex [La(NO$_3$)$_3$L]," J. C. S. Chem. Comm, 774–775 (1979).

8. Khalil K Abid et al., "The Template Synthesis and Crystal and Molecular Structure of a Sexidentate Schiff-base Macrocyclic Complex of Samarium(III), [Sm(C$_{18}$H$_{18}$N$_6$)(NO$_3$)(OH)(H$_2$O)]NO$_3$ 2MeOH," J. Chem. Soc. Dalton Trans., 351–354 (1984).

9. Genglin Wang, et al., "Lanthanide Complexes with Eighteen-Membered Hexaaza Macrocyclic Ligands" (Dep. Chem., Nankai Univ., Tianjin, Peop. Rep. China). Gaodeng Xuexiao Huaxue Xuebao 1984, 5(3), 281–6 (Ch).

The strategy of joining paramagnetic metals with chelators has been used in the past for making MRI contrast agents. However, because the metal is surrounded by the chelator molecules, the interactions of the unpaired electrons with the water protons are reduced. Consequently, the ability of the metal-chelator complex to increase water relaxation rates is diminished. Thus, it is surprising that the complexes of the present invention which have been tested in vitro increase water relaxation rates to about the same extent as the metal by itself. When tested in vivo, the present invention may provide the effectiveness of the metal alone without the toxicity problem of the metal alone.

The term "magnetic resonance images" is intended to apply to both MRI images and MRS images. The terms "MRI images" and "MRS images" are used when it is desired to distinguish between magnetic resonance imaging and magnetic resonance spectroscopy. Contrast agents of this invention may be used in imaging solid materials, such as polymers and ceramics. The frequency range of radiation used in MRI and MRS will range from about 0.1 MHz to about 1.0 GHz. A contrast agent may be injected into a living being by means of a needle or passed into a body orifice. In some instances, it is desirable to add a contrast agent to the object while the image of the object is being formed. In addition to being dissolved in sterile aqueous solution for administration, a contrast agent may be administered in other biocompatible solutions, such as oils. For example, a contrast agent may be in Fruend's Adjuvant or encapsulated in a liposome.

The foregoing has been presented for purposes of illustration and description. It is not intended to be exhaustive or to limit the invention to the precise form disclosed. It is intended that the scope of the invention be defined by the claims.

What is claimed is:

1. A method of enhancing contrast of a magnetic resonance image of a living organism by incorporating a contrast agent into the organism, in an amount effective to enhance contrast of the image, prior to forming the image or during formation of the image, where said contrast agent is a paramagnetic lanthanide hexaazamacrocyclic molecule and has the structural formula

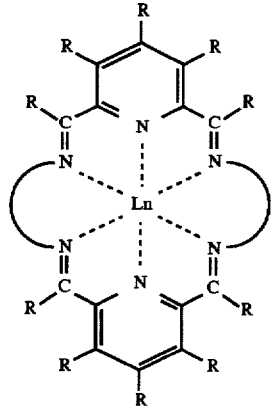

where the symbol

and the symbol

denotes a constituent of the contrast agent chosen from a group consisting of five constituents having the structures

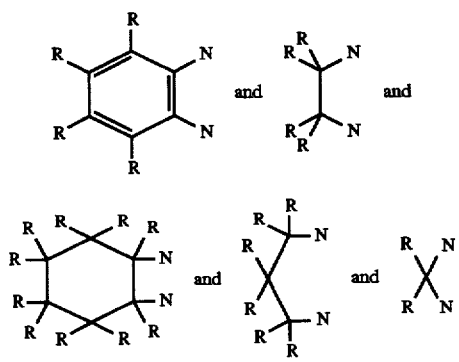

and where R represents a hydrogen atom or a substituent group chosen from a class consisting of alkyl, alkoxy, acyl, aroxy, alkylamine, aryl, hydroxy, aryloxy, amine, carboxylate, phosphate, and sufonate groups.

2. The method of claim 1 where said contrast agent is in aqueous solution.

3. The method of claim 1 where said contrast agent is incorporated in said object by injection.

4. The method of claim 1 where said contrast agent is incorporated in said object by passing said contrast agent into a body orifice.

5. The method of claim 1 where said lanthanide is gadolinium.

6. The method of claim 1 wherein said contrast agent has the structural formula:

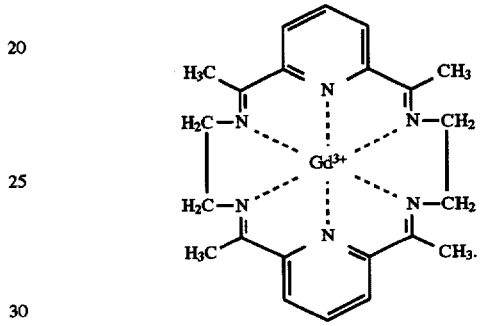

* * * * *